United States Patent [19]

Derlien

[11] 4,180,067
[45] Dec. 25, 1979

[54] APPARATUS FOR DELIVERING FLUIDS WITH CONTROLLED RATES OF FLOW

[75] Inventor: Michael L. Derlien, Wembley, England

[73] Assignee: Pye (Electronic Products) Limited, Cambridge, England

[21] Appl. No.: 836,790

[22] Filed: Sep. 26, 1977

[30] Foreign Application Priority Data

Sep. 28, 1976 [GB] United Kingdom ............... 40187/76

[51] Int. Cl.² .............................................. A61M 05/00
[52] U.S. Cl. .............................. 128/214 F; 128/218 R; 128/234; 222/389
[58] Field of Search ........... 128/214 R, 214 E, 214 F, 128/214 Z, 218 R, 218 A, 230, 234, 273; 222/389; 92/129, 130 B

[56] References Cited

U.S. PATENT DOCUMENTS

| | | | |
|---|---|---|---|
| 2,865,371 | 12/1958 | Dorbecker et al. | 128/214 F |
| 3,349,767 | 10/1967 | Gidlund | 128/218 R |
| 3,815,481 | 6/1974 | Pauliukonis | 92/130 B |
| 3,888,239 | 6/1975 | Rubinstein | 128/234 X |
| 4,132,332 | 1/1979 | Wassiliett | 222/389 X |

FOREIGN PATENT DOCUMENTS 1449504 9/1976 United Kingdom .

*Primary Examiner*—Dalton L. Truluck
*Attorney, Agent, or Firm*—Thomas A. Briody; Edward J. Connors, Jr.; Jack E. Haken

[57] ABSTRACT

An apparatus for delivering fluid at a controlled rate of flow wherein fluid is forced from a container by the piston of a vacuum cylinder. A flow restricting valve is provided, either at the output of the container or at the output of a second cylinder which is coupled to the piston of the vacuum cylinder.

5 Claims, 3 Drawing Figures

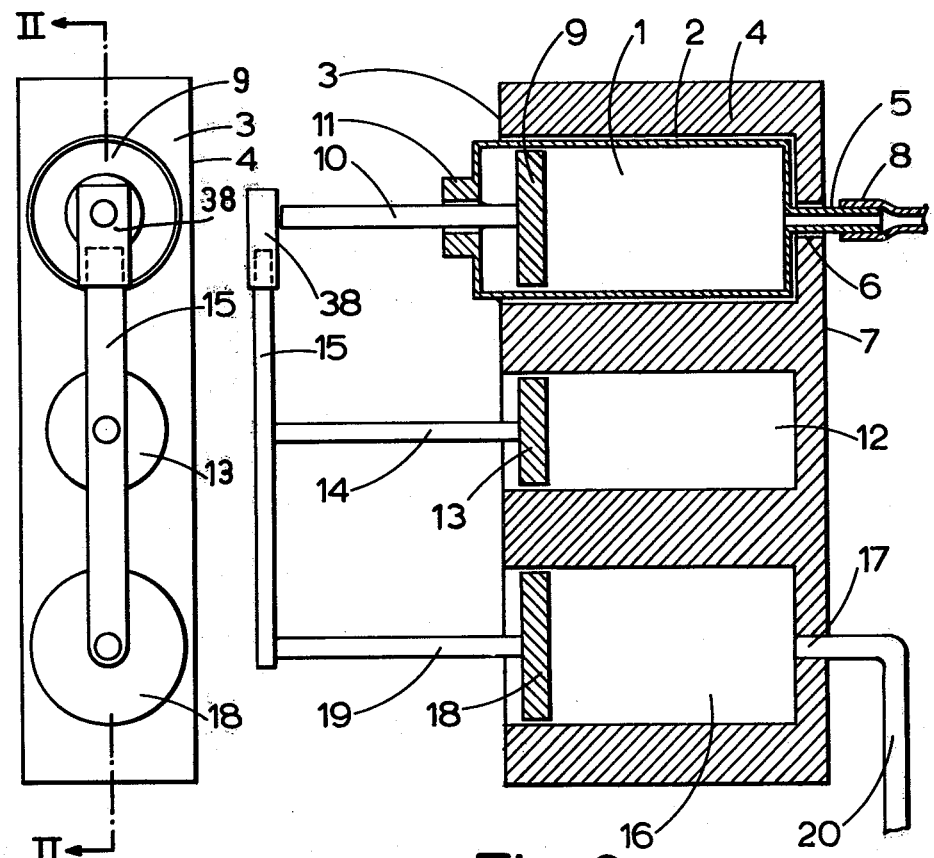
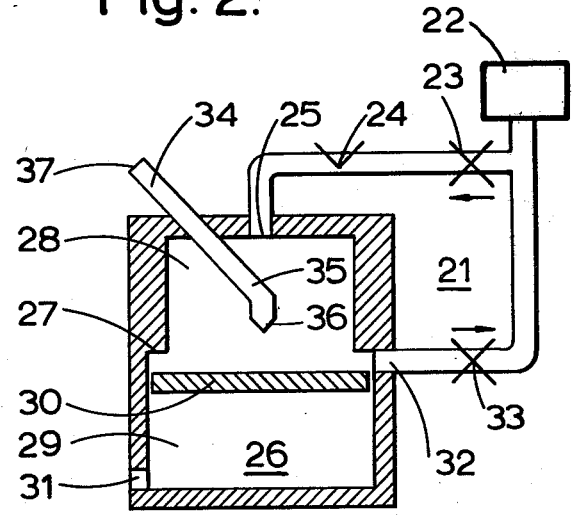
Fig. 1.
Fig. 2.
Fig. 3.

APPARATUS FOR DELIVERING FLUIDS WITH CONTROLLED RATES OF FLOW

This invention relates to apparatus for delivering fluid with controlled rates of flow, for example for the parenteral administration of medical fluids, which includes a storage container the volume of which can be reduced by means of an actuator so as to supply fluid to an outlet tube.

The usual procedure for delivering fluids with a controlled rate of flow, for example, in the gradual parenteral administration of biological fluids, such as blood, plasma or medicinal solutions, such as drugs into the human body, was to use gravity-operated apparatus such as an intravenous infusion set. An intravenous infusion set comprises a bottle for the fluid which is supported in an inverted position at a higher level than the patient, an intravenous feed tube, typically of a plastic material and a restrictor mechanism, such as, a clamp operating on the plastic tube, the clamp being adjusted so as to allow the fluid to drip at a controlled rate into a drip chamber located below the bottle. The drip chamber allows a nurse or other attendant to observe the rate of flow of fluid from the bottle and to adjust the restrictor to give a desired rate. It also creates a reservoir for the fluid at the lower end of the chamber to ensure that no air enters the main feeding tube leading to the patient.

The intravenous infusion set has the virtues of simplicity, of independence from external power supplies and a capacity for adjustment over a wide range of flow rates. It has nevertheless a number of shortcomings. For various reasons, including change of level of the liquid in bottle, change of temperature and drift in effective restrictor setting caused, for example, by creep changes in the plastic tube, the known intravenous infusion set is subject to variations in flow rate produced. Furthermore, as the delivery pressure is necessarily fairly low when the drip chamber and restrictor are mounted at a convenient height, the flow rate is also dependent on variations in any back pressure acting on the liquid and which may be due to changes in the patient's venous or arterial pressure or by movement of the patient, etc. It is clear that any substantial variation of the flow rate from its desired value may endanger the patient, or at least cause an adverse effect on the treatment and consequential discomfort. It is therefore necessary for a nurse or an attendant to monitor the actual flow rate of the fluids delivered by an intravenous infusion set, at frequent intervals and to reset the restrictor as may be found necessary to maintain the desired rate.

A further disadvantage is that the necessity for maintaining the bottle for the fluid at a substantially constant height above the patient renders the apparatus inconvenient for mobile use.

Equipment has been devised to give better control of flow rate. For example, a pump may be employed whose delivery rate is a function of its speed, powered by a drive unit comprising a servo control system adapted to maintain a feedback signal representative of the actual delivery rate substantially equal to a control signal representative of the desired rate. In another arrangement, a disposable syringe is provided with a linear actuator such as a screw and nut, the actuator being driven by a servo-controlled unit at a speed adapted to produce a desired flow rate. While such devices largely overcome the difficulty of an unstable flow rate, this is at the cost of much greater complexity as compared with the simple intravenous infusion set, together with a dependence on external power supplies. Such equipments are consequently more costly, more liable to failure and are also unsuited to mobile use.

Self-contained infusion units are known comprising a pump unit, e.g. a peristaltic pump, driven by a spring-powered mechanism provided with a constant-speed escapement. Such units can provide a substantially constant feed rate, but cannot easily be adapted to provide any desired rate within a wide range of rates. One object of the present invention is to mitigate the aforesaid disadvantages.

A further object of the present invention is to provide an apparatus which is capable of adjustment to provide any one of a wide range of flow rates and which is simple in construction, self contained in use in that no external power supply is needed when the apparatus is set and is suited for both static and mobile use.

According to the present invention the actuator comprises at least one cylinder which is closed at one end having a piston slidable therein, said piston being coupled via a transmission to a movable wall of the storage container, the cylinder being evacuated when the slidable piston is substantially at the open end of the cylinder so that atmospheric pressure acts upon the piston to drive it towards the closed end of the cylinder, said motion via the transmission producing a reduction of the volume of the storage container.

The fluid is preferably delivered to the outlet tube under constant pressure.

An adjustable flow restrictor valve may be provided in the outlet tube which can be adjusted to control the flow of fluid from the syringe storage.

In one preferred embodiment the actuator comprises, in addition to the first cylinder having the first piston, a second cylinder with a second piston slidable therein, the second piston being coupled to the first piston for motion therewith, which second cylinder is filled with an auxiliary fluid when the second piston is substantially at the open end of the second cylinder and has an outlet port at the other end of the second cylinder which is connected to an adjustable flow restrictor valve with which the rate of movement of the second piston and also of the first piston coupled thereto may be controlled.

No restrictor valve is required in the outlet tube of this embodiment of the invention.

In order that the invention and the manner in which it is to be performed may more easily be understood, an embodiment thereof will now be described, by way of example, with reference to the attached drawings, of which:

FIG. 1 is a plan view of the apparatus according to the invention

FIG. 2 is a sectional view of the apparatus according to the invention taken on the line II—II of FIG. 1, and FIG. 3 is a partially sectional view of a flow restricting and monitoring assembly for use with the apparatus of FIG. 1.

Referring to FIGS. 1 and 2, a storage container in the form of a disposable syringe 1, containing infusion fluid is removably housed in a cavity 2 which extends from a face 3 of a substantially rectangular frame or block 4 of a substantially rigid material such as, a thermosetting plastics, a glass or a metal material. The syringe 1 has an outlet tube 5 which passes through a hole 6 provided between the base of the cavity 2 and the face 7 of the block 4. An intravenous feed tube 8 is connected to the outlet tube 5 outside the block 4. The syringe 1 is provided with a plunger 9 and plunger activating rod 10 passing through a gland 11 in the top of the syringe and extending beyond the face 3 of the block 4. The block 4 further comprises a first cylinder 12 having an open end facing the face 3 and a closed end facing the rear face 7. A first piston 13, slidable within the cylinder 12 is in sealing relationship with the cylinder wall. Typically, a seal of a rolling diaphragm type (not shown in the drawings) is provided between the piston 13 and the wall of the cylinder 12. A first piston rod 14 extending beyond the face 3 of the block 4 connects the piston 13 to a cross-head 15 which functions as a transmission mechanically coupling the piston 10 to the movable plunger 9 of the storage container or syringe 1. FIG. 2 illustrates the case where the rod 10 is releasably connected to the cross-head 15 as hereinafter described.

It is arranged that when the piston 13 is at the closed end of the cylindrical cavity 12, the volume of the clearance space between the piston and the cylinder is relatively very small compared with the total volume of the cylinder 12. Consequently, when the piston 13 is moved to a position adjacent the open end of the cylinder 12 (to the left in FIG. 2), a high degree of vacuum is formed in the part of the cylinder swept by the piston. Since the outer face of the piston 13 is exposed to atmospheric pressure ($P_1$), there is a resultant thrust T on the piston 13 given by $T=P_1 A_1$ where $A_1$ is the area of the piston. The value of T is substantially constant, and independent of the position of the piston 13 except when the piston again approaches closely to the closed end of cylinder 12.

When the piston 13 is at the open left hand end of the cylinder 12 and the syringe 1 is filled with infusion fluid (i.e. the plunger 9 is at the top of the syringe), the cross-head 15 bears on the end of the plunger actuating rod 10. The thrust T can drive the piston 13 into the cylinder 12. The resulting movement of the cross-head 15 drives the plunger actuating rod 10 and plunger 9 into the cavity 2 of the syringe 1. If a flow-regulating second cylinder as described below is not provided, then the cross-head movement will cause infusion fluid to be delivered under a constant pressure $P_2$ equal to $T/A_2$ where $A_2$ is the area of the plunger 9.

If desired, the rate of delivery of the fluid may be controlled by means of a restrictor valve of a known type provided in the feed tube 8. In a preferred arrangement, however, no impediment is placed in the path of the infusion fluid from the syringe to the patient. A separate fluid circuit is provided for controlling and monitoring the flow rate.

In a preferred arrangement, a second cylinder 16 in addition to the cavity 2 for the disposable syringe 3 and the first cylinder 12 for the actuator is provided in the block 4, extending from the face 3 towards the rear face 7 of the block 4. A port 17 extends from the base of the cylinder 16 to the face 7. A second piston 18, slidable within the cylindrical cavity 16 is in sealing relationship with the cylinder wall, e.g. by use of a rolling diaphragm type seal (not shown). A second piston rod 19 connects the piston 18 to the crosshead 15.

The second cylinder 16 is preferably filled with an inert auxiliary liquid, e.g. water.

The thrust T on the first piston 13 is communicated via the cross-head 15 and piston rod 19 to the piston 18, driving the latter into the cylindrical cavity 16 and so expelling liquid through the port 17. The port 17 is connected via a tube 20 to a flow restricting and monitoring unit 21 to be described hereinafter with reference to FIG. 3, which is effective to control the rate at which liquid is expelled from the cylinder 16. This in turn controls the rate of movement of the piston 18. Since the first piston 13 and the plunger 9 are coupled they move second piston 18, and therefore the rate of delivery of infusion fluid from the syringe 1 is also controlled. In the arrangement shown the first piston 13, the plunger 9 and the second piston 18 are coupled so as to move at the same rate. The thrust of the plunger actuating rod 10 against the cross-head 15 will be small because no restrictor valve is placed in the infusion fluid path, and as a result the pressure of the auxiliary fluid is constant and equals $P_3=P_1 A_1/A_3$, where $A_1$ is the cross-sectional area of the first piston 13, $A_3$ is the cross-sectional area of the second piston 18 and $P_1$ is the atmospheric pressure.

With reference to FIG. 3, the flow restricting and monitoring unit 21 has means to adjust the rate of flow which unit has an inlet 22 connectable to the port 17 (FIG. 2) of the cylinder 16 by the tube 20.

Auxiliary liquid entering the inlet 22 passes through a non-return valve 23 which may be of the spring-loaded ball type, and a flow restrictor 24 which may for example be a needle valve with screw adjustment, to a port 25 provided in the upper end of a cylindrical chamber 26.

The wall of the chamber 26 has a step 27 such that the upper portion 28 of the chamber is smaller in diameter than the lower portion 29. A third piston 30 is free to move within the lower portion 29 of the chamber 26 but is prevented from entering the upper portion by the step 27. The piston 30 is in sealing relation with the wall of the lower portion 29. Typically a rolling diaphragm type seal (not shown) is employed.

The space below the piston 30 is vented to atmosphere through an exhaust port 31. A port 32 in a sidewall of the chamber 26 at the level of the step 27 is connected to the inlet 22 through a non-return valve 33 such that liquid can pass from the port 32 to the inlet 22 but not in the reverse direction.

A rod 34 of perspex or other transparent material extends through the top of the chamber 26 and has an end portion 35, at an angle to the remainder of the rod so as to extend vertically downwards below the port 25. The end portion 35 is provided with a conical downward-pointing tip 36.

Before delivery of infusion fluid commences, i.e. when the pistons 13 and 18 are adjacent the open ends of their respective cylinders, the piston 30 is at the top of its stroke, bearing against the step 27. As delivery progresses, liquid expelled from the cylinder 16 enters the unit 21 via the inlet 22 and passes through the non return valve 23 and the flow restrictor 24 to the port 25 at a rate determined by the setting of the restrictor 24. From the port 25 the liquid falls on the end portion 35 of the rod 34 and drips from the conical tip 36.

The rod serves as an optical tube, and as such successive drop of liquid grows on and subsequently falls from the conical tip 36, the opposite end 37 of the rod, outside the chamber 26, shows alternately light and dark. Thus the rate of drop formation may readily be observed. As has been shown hereinbefore, this rate of drop formation, which is dependent on the setting of the adjustable flow restrictor 24, is a measure of the rate of delivery of infusion fluid from the syringe 1. Known means of monitoring the rate at which the liquid is expelled from the cylinder 16 may be used if desired. In the aforesaid method as the drops of liquid fall on the piston 30, the latter descends in the chamber 26 to provide space to accommodate the accumulating liquid. At the end of the infusion, when the piston 13, and with it the piston 18 and the syringe plunger 9 have reached end of their respective strokes, the liquid displaced from the cylindrical cavity 16 is collected above the third piston 30 in the lower portion 29 of the chamber 26. In preparation for a fresh infusion, the cross-head 15 is then withdrawn to bring the pistons 13 and 18 substantially to the open ends of their respective cylinders. The liquid in the chamber 26 is drawn through the port 32, the non-return valve 33, the inlet 22 and the tube 20 to the cylinder 16 and the piston 30 rises in the chamber 26 until it again rests against the step 27. Thus the flow restriction and monitoring unit forms a closed system which does not require re-charging with liquid for each successive infusion. An advantage, as compared with systems in which an adjustable flow restrictor is placed in the path of the infusion fluid is that it permits the use of an inert liquid, e.g. water, which, unlike some infusion fluids, has no tendency to form deposits and clog or block small passageways. Hence an accurate and reproducible control of flow at even very low flow rates can be obtained.

A further advantage relates to the re-setting of the actuator in readiness for a further infusion. The cross-head 15 may be drawn back by hand, but if the value of the thrust T is great, i.e. the area of the piston 13 is large, this may be a matter of some difficulty. When a supply of gas(air) under pressure is available, a particularly convenient way of resetting the actuator is to apply sufficient gas pressure momentarily to the underside of the piston 30 via the exhaust port 31. This forces up the piston 30, driving the auxiliary liquid through the non-return valve 33 into the cylinder 16, so forcing back the piston 18 and with it the cross-head 15 and the piston 13. The piston 18 may then be held in this position until required for use by preventing liquid from flowing through the port 25 by closing the flow restrictor 24.

When the cross-head 15 has been drawn or forced back, the disposable syringe 1 may be replaced by a loaded syringe. The end 38 of the cross-head 15 may be made detachable to facilitate changing the syringe.

It will be apparent that instead of a disposable syringe, a syringe which is re-charged after each infusion may be employed. In this case the plunger actuating rod 10 is rigidly connected to the cross-head 15. To re-charge the syringe, the feed tube 8 is disconnected from the outlet tube 5 and a source of infusion fluid connected thereto, so that fluid is drawn into the syringe when the cross-head is drawn back. As a further alternative, a part of the syringe body 1 may be omitted so that the plunger 9 is arranged in sealing relationship with the wall of the cavity 2. In this case the block 4 is made of a substance such as stainless steel or glass which is inert to the infusion fluid.

For convenience of illustration, the flow restricting and monitoring unit 21 has been shown in the drawings as a separate unit. It will be appreciated that the cavity 26 may be provided within the block 4, the non-return valves 23 and 33 and the flow restrictor valve 24 being housed in suitable passageways provided in the block 4.

I claim:

1. An apparatus for delivering fluid with controlled rates of gradual flow from a removable container placed in the apparatus, comprising a frame having a cavity adapted for housing a removable storage container having a movable wall and an outlet tube, the volume of which container can be reduced by movement of the wall so as to supply fluid to the outlet tube;

at least one first cylinder arranged in the frame and closed at one end;

a first piston slidably disposed within and in sealed engagement with the first cylinder, the first cylinder being evacuated when the first piston is substantially at the open end of the first cylinder so that atmospheric pressure acts upon the first piston to drive it towards the closed end of the first cylinder, and means for coupling said first piston to the movable wall of a storage container placed in the cavity for movement of the wall responsive to movement of the first piston toward the closed end of the first cylinder, so arranged that said piston movement produces a reduction of the volume of the storage container.

2. An apparatus according to claim 1 comprising at least one said removable storage container housed in said cavity, and an adjustable flow restrictor valve connected to said outlet tube for control of the flow of fluid delivered from the storage container.

3. An apparatus for delivering fluid with controlled rates of flow, comprising a storage container having a movable wall and an outlet tube, the volume of which container can be reduced by movement of the wall by means of an actuator so as to supply fluid to the outlet tube, wherein the actuator comprises:

at least one first cylinder which is closed at one end;

a first piston slidably disposed within and in sealed engagement with the first cylinder, the first cylinder being evacuated when the first piston is substantially at the open end of the first cylinder so that atmospheric pressure acts upon the first piston to drive it toward the closed end of the first cylinder;

a second cylinder having an open end and an outlet port at the other end, and a second piston slidably disposed within said second cylinder, said second cylinder being filled with an auxiliary fluid when the second piston is substantially at the open end of the second cylinder;

an adjustable flow restrictor valve connected to said outlet port, for controlling the rate of movement of the second piston;

means for coupling said second piston to said first piston for movement therewith from the respective open end toward the respective other end of the cylinders, and means for coupling said first piston to the movable wall of the storage container for movement of the wall responsive to movement of the first piston towards the closed end of the first cylinder, so arranged that said first piston movement produces a reduction of the volume of the storage container.

4. An apparatus according to claim 3 wherein said storage container is a removable injection syringe, and the movable wall is a plunger having a rod extending therefrom for engagement by said means for coupling said first piston to the movable wall.

5. An apparatus as claimed in claim 4 wherein said means for coupling said first piston to the movable wall provides detachable coupling, and includes a member disposed to butt against an end of the rod.

* * * * *